United States Patent
Kruck et al.

(10) Patent No.: US 11,865,201 B2
(45) Date of Patent: Jan. 9, 2024

(54) PRODUCT FOR DYEING KERATINOUS MATERIAL, CONTAINING AMINOSILICONE, A CHROMOPHORIC COMPOUND AND ETHOXYLATED FATTY ACID ESTER

(71) Applicant: Henkel AG & Co. KGaA, Duesseldorf (DE)

(72) Inventors: Constanze Kruck, Grevenbroich (DE); Melanie Moch, Dormagen (DE); Sandra Hilbig, Bochum (DE); Daniela Kessler-Becker, Leverkusen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 0 days.

(21) Appl. No.: 17/762,655

(22) PCT Filed: Jul. 13, 2020

(86) PCT No.: PCT/EP2020/069764
§ 371 (c)(1),
(2) Date: Mar. 22, 2022

(87) PCT Pub. No.: WO2021/058158
PCT Pub. Date: Apr. 1, 2021

(65) Prior Publication Data
US 2022/0354769 A1    Nov. 10, 2022

(30) Foreign Application Priority Data
Sep. 23, 2019   (DE) .......................... 102019214466.7

(51) Int. Cl.
*A61Q 5/10*   (2006.01)
*A61K 8/898*   (2006.01)
*A61K 8/37*   (2006.01)
*A61Q 5/06*   (2006.01)

(52) U.S. Cl.
CPC ................ *A61K 8/898* (2013.01); *A61K 8/37* (2013.01); *A61Q 5/065* (2013.01); *A61K 2800/43* (2013.01); *A61K 2800/438* (2013.01); *A61K 2800/4324* (2013.01)

(58) Field of Classification Search
CPC ...... A61K 8/898; A61K 8/37; A61K 2800/43; A61K 2800/4324; A61K 2800/438; A61K 8/39; A61K 8/86; A61K 8/922; A61Q 5/065
USPC ............................................................ 8/405
See application file for complete search history.

(56) References Cited

U.S. PATENT DOCUMENTS

2017/0172901 A1 *   6/2017   Kerl .......................... A61K 8/22

FOREIGN PATENT DOCUMENTS

| DE | 102014221536 A1 * | 4/2016 | ............. A61Q 5/065 |
| DE | 102018222022 A1 * | 6/2020 | ............. A61Q 5/10 |
| DE | 102018222024 A1 * | 6/2020 | ............. A61Q 5/10 |
| WO | 2014044602 A2 | 3/2014 | |
| WO | 2015090804 A1 | 6/2015 | |
| WO | 2018206453 A1 | 11/2018 | |
| WO | WO 2018/206453 A1 * | 11/2018 | ............. A61Q 5/065 |

* cited by examiner

*Primary Examiner* — Eisa B Elhilo
(74) *Attorney, Agent, or Firm* — Lorenz & Kopf, LLP

(57) ABSTRACT

Agents and methods for coloring keratinous material, in particular human hair, are provided. In one example, the agent includes (a1) at least one amino-functionalized silicone polymer, (a2) at least one color-imparting compound, and (a3) at least one addition product of ethylene oxide to the esters of $C_{12}$-$C_{24}$ fatty acids and $C_1$-$C_{12}$ aliphatic alcohols.

19 Claims, No Drawings

PRODUCT FOR DYEING KERATINOUS MATERIAL, CONTAINING AMINOSILICONE, A CHROMOPHORIC COMPOUND AND ETHOXYLATED FATTY ACID ESTER

CROSS-REFERENCE TO RELATED APPLICATION

This application is a U.S. National-Stage entry under 35 U.S.C. § 371 based on International Application No. PCT/EP2020/069764, filed Jul. 13, 2020, which was published under PCT Article 21(2) and which claims priority to German Application No. 102019214466.7, filed Sep. 23, 2019, which are all hereby incorporated in their entirety by reference.

TECHNICAL FIELD

The present application relates to an agent for coloring keratinous material, in particular human hair, which includes at least one amino-functionalized silicone polymer (a1), at least one coloring compound (a2) and at least one addition product of ethylene oxide onto the esters of $C_{12}$-$C_{24}$ fatty acids and aliphatic $C_1$-$C_{12}$ alcohols (a3).

A second object of this application is a method for dyeing keratinous material, in particular human hair, wherein an agent of the first object of the present disclosure is applied to the keratinous material, allowed to act and then washed out again with water.

BACKGROUND

Changing the shape and color of keratinous material, especially human hair, is a key area of modern cosmetics. To change the hair color, the expert knows various coloring systems depending on the coloring requirements. Oxidation dyes are usually used for permanent, intensive dyeings with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeings obtained with direct dyes have a shorter shelf life and quicker wash ability. Dying's with direct dyes usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents including surfactants. Various products of this type are available on the market under the name hair mascara.

If the user wants particularly long-lasting dyeings, the use of oxidative dyes has so far been his only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. In particular, the color intensities and wash fastnesses of dyes based on the use of pigments still need to be improved.

It was the task of the present disclosure to provide a dyeing system which has color intensities comparable to oxidative dyeing wherever possible. However, the oxidation dye precursors normally used for this purpose should not be used. A technology was sought that would make it possible to fix the colorant compounds known from the prior art (such as pigments in particular) to the hair in an extremely durable manner. When using the agents in a dyeing process, particularly intensive dyeing results with good fastness properties should be achieved. In addition, the agents should also have improved gray coverage.

BRIEF SUMMARY

Agents and methods for dyeing keratinous material, in particular human hair, are provided. In an exemplary embodiment, the agent includes (a1) at least one amino-functionalized silicone polymer, (a2) at least one color-imparting compound, and (a3) at least one addition product of ethylene oxide to the esters of $C_{12}$-$C_{24}$ fatty acids and $C_1$-$C_{12}$ aliphatic alcohols.

In another embodiment, the method includes applying the agent to the keratinous material. The agent is exposed to the keratinous material for a period from about 30 seconds to about 15 minutes. The agent is rinsed out from the keratinous material with water.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

Surprisingly, it has now been found that the above problem can be excellently solved if keratinous materials, in particular hair, are colored with an agent including at least one amino-functionalized silicone polymer (a1), at least one coloring compound (a2), and at least one addition product of ethylene oxide with the esters of $C_{12}$-$C_{24}$ fatty acids and aliphatic $C_1$-$C_{12}$ alcohols (a3).

A first object of the present disclosure is an agent for coloring keratinous material, in particular human hair, including.

(a1) at least one amino-functionalized silicone polymer, and
(a2) at least one color-imparting compound, and
(a3) at least one addition product of ethylene oxide to the esters of $C_{12}$-$C_{24}$ fatty acids and $C_1$-$C_{12}$ aliphatic alcohols In the course of the work carried out on the present disclosure, it has been surprisingly shown that the use of an ethoxylated fatty acid ester (a3) in an agent including an amino silicone (a1) as well as a coloring compound (a2) leads to an improvement in color intensity when this agent is applied in a dyeing process on the keratinous material, in particular on human hair. These positive effects were observed when the colorant compound (a2) was a pigment.

Keratinic Material

Keratinous material includes hair, skin, nails (such as fingernails and/or toenails). Wool, furs and feathers also fall under the definition of keratinous material.

Preferably, keratinous material is understood to be human hair, human skin and human nails, especially fingernails and toenails. Keratinous material is understood to be human hair.

Coloring Agent

The term "coloring agent" is used in the context of the present disclosure for a coloring of the keratin material, of the hair, caused using coloring compounds, in particular pigments. In this coloring process, the pigments are deposited as coloring compounds in a particularly homogeneous, uniform and smooth film on the surface of the keratin material.

Amino-Functionalized Silicone Polymers (a1)

As the first ingredient (a1) essential to the present disclosure, the agent includes at least one amino-functionalized silicone polymer. The amino-functionalized silicone polymer may alternatively be referred to as amino silicone or amodimethicone.

Silicone polymers are macromolecules with a molecular weight of at least 500 g/mol, preferably at least 1000 g/mol, more preferably at least 2500 g/mol, particularly preferably at least 5000 g/mol, which include repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than $10^7$ g/mol, preferably not more than $10^6$ g/mol, and particularly preferably not more than $10^5$ g/mol.

The silicone polymers include many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, beneficial effects could be obtained with amino-functionalized silicone polymers (a1) if they carry at least one primary, at least one secondary and/or at least one tertiary amino group. However, dyeings with the best wash fastness were observed when an amino-functionalized silicone polymer (a1) was used in agent (a), which includes at least one secondary amino group.

In a very particularly preferred embodiment, an agent as contemplated herein is wherein it includes at least one amino-functionalized silicone polymer (a1) having at least one secondary amino group.

The secondary amino group(s) may be located at various positions on the amino-functionalized silicone polymer. Particularly beneficial effects were found when an amino-functionalized silicone polymer (a1) was used that has at least one, preferably several, structural units of the formula (Si amino).

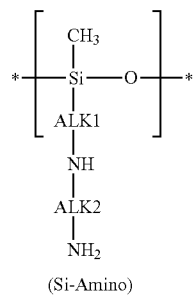

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, an agent as contemplated herein is wherein it includes at least one amino-functionalized silicone polymer (a1) including at least one structural unit of the formula (Si amino),

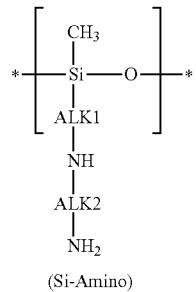

(Si-Amino)

where
ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A divalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a1), so that the silicone polymer includes multiple structural units of the formula (Si amino).

Particularly well-suited amino-functionalized silicone polymers (a1) with at least one secondary amino group are listed below.

Dyeings with the best wash fastnesses could be obtained if in the process as contemplated herein at least one agent (a) was applied to the keratinous material which includes at least one amino-functionalized silicone polymer (a1) including structural units of the formula (Si-I) and of the formula (Si-II)

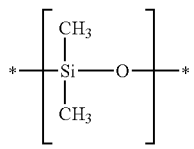

(Si-I)

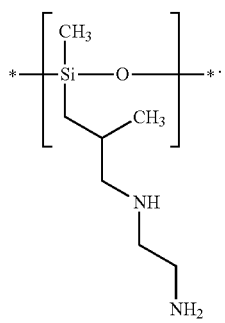

(Si-II)

In a further explicitly quite particularly preferred embodiment, an agent as contemplated herein is wherein it includes at least one amino-functionalized silicone polymer (a1) including structural units of the formula (Si-I) and of the formula (Si-II)

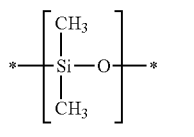

(Si-I)

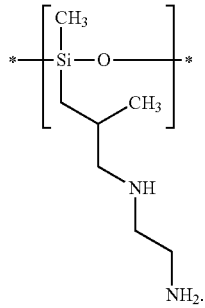

(Si-II)

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-1(2-aminoethypaminol-2-methylpropyl Me, Di-Me-Siloxane" and the CAS number 106842-44-8.

In another preferred embodiment, an agent as contemplated herein is wherein it includes at least one amino-functional silicone polymer (a1) of the formula of the formula (Si-III),

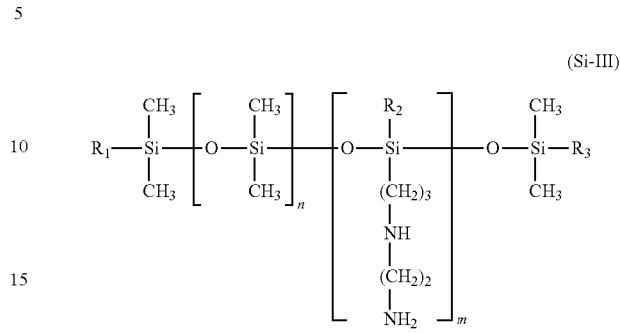

(Si-III)

where
m and n mean numbers chosen so that the sum (n+m) is in the range 1 to 1000,
n is a number in the range 0 to 999 and m is a number in the range 1 to 1000,
R1, R2 and R3, which are the same or different, denote a hydroxy group or a C1-4 alkoxy group,
wherein at least one of R1 to R3 represents a hydroxy group;

A further agent preferred as contemplated herein is wherein it includes at least amino-functional silicone polymer (a1) of the formula of the formula (Si-IV),

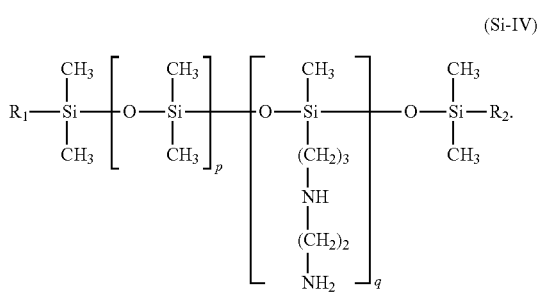

(Si-IV)

located in the
p and q mean numbers chosen so that the sum (p+q) is in the range 1 to 1000,
p is a number in the range 0 to 999 and q is a number in the range 1 to 1000,
R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si(CH$_3$)$_2$ group is necessarily bonded to an —[O—Si(CH$_3$)$_2$] grouping.

Agents as contemplated herein which contain at least one amino-functional silicone polymer (a1) of the formula (Si-V) have also proved to be particularly effective with respect to the desired effects

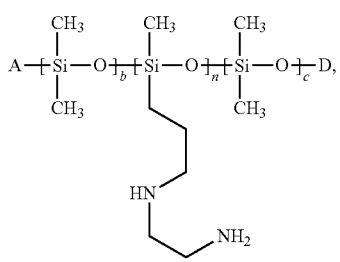

(Si-V)

located in the

A represents a group —OH, —O—Si(CH$_3$)$_3$, —O—Si(CH$_3$)$_2$OH, —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, b, n and c stand for integers between 0 and 1000, with the specifications n>0 and b+c>0 at least one of the conditions A=—OH or D=—H is fulfilled.

In the above formula (Si-V), the individual siloxane units are statistically distributed with the indices b, c and n, i.e., they do not necessarily have to be block copolymers.

Agent (a) may further include one or more different amino-functionalized silicone polymers represented by the formula (Si-VI)

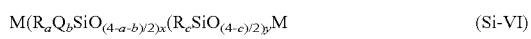   (Si-VI)

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical including at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2,000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical including from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional residue including at least one amino functional group. One formula for Z is NH(CH$_2$)$_z$NH$_2$, where z is 1 or more. Another formula for Z is —NH(CH$_2$)$_z$(CH 2)$_{zz}$NH, wherein both z and zz are independently 1 or more, this structure comprising diamino ring structures, such as piperazinyl. Z is most preferably an —NHCH$_2$CH$_2$NH$_2$ residue. Another formula for Z is —N(CH$_2$)$_z$(CH$_2$)$_{zz}$NX$_2$ or —NX$_2$, wherein each X of X$_2$ is independently selected from the group of hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$ SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, an agent as contemplated herein is wherein it includes at least one amino-functional silicone polymer of the formula (Si-VII)

   (Si-VII), wherein means:

G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;

a stands for a number between 0 and 3, especially 0;

b stands for a number between 0 and 1, especially 1, m and n are numbers whose sum (m+n) is between 1 and 2000, preferably between 50 and 150, where n preferably assumes values from 0 to 1999 and from 49 to 149 and m preferably assumes values from 1 to 2000, from 1 to 10, R' is a monovalent radical selected from -Q-N(R")—CH$_2$—CH$_2$—N(R")$_2$
-Q-N(R")$_2$
-Q-N$^+$(R")$_3$A$^-$
-Q-N$^+$H(R")$_2$A$^-$
-Q-N$^+$H$_2$(R")A$^-$
-Q-N(R")—CH$_2$—CH$_2$—N$^+$R"H$_2$A$^-$, where each Q is a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—, R" represents identical or different radicals selected from the group of —H, -phenyl, -benzyl, —CH$_2$—CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In another preferred embodiment, an agent as contemplated herein is exemplified by including at least one amino-functional silicone polymer (a1) of the formula (Si-VIIa),

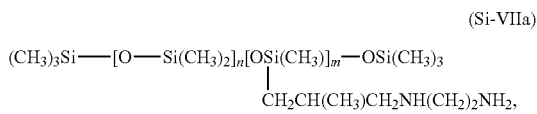
(Si-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In the context of a further preferred embodiment, an agent as contemplated herein is wherein it includes at least one amino-functional silicone polymer (a1) of the formula (Si-VIIb)

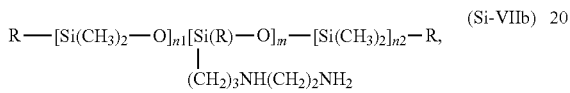
(Si-VIIb)

in which R represents —OH, —O—CH$_3$ or a —CH$_3$ group and m, n1 and n2 are numbers whose sum (m+n1+n2) is between 1 and 2000, preferably between 50 and 150, the sum (n1+n2) preferably assuming values from 0 to 1999 and from 49 to 149 and m preferably assuming values from 1 to 2000, from 1 to 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above 0.25 meq/g, preferably above 0.3 meq/g and above 0.4 meq/g. The amine number represents the milliequivalents of amine per gram of the amino-functional silicone. It can be determined by titration and also expressed in the unit mg KOH/g.

Furthermore, agent (a) including a special 4-morpholinomethyl-substituted silicone polymer (a1) are also suitable. This amino-functionalized silicone polymer includes structural units of the formulae (SI-VIII) and of the formula (Si-IX)

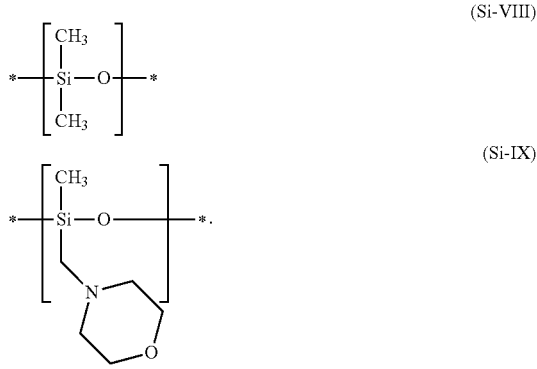

Corresponding 4-morpholinomethyl-substituted silicone polymers are described below.

A very particularly preferred amino-functionalized silicone polymer is known by the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

(Si-VIII)

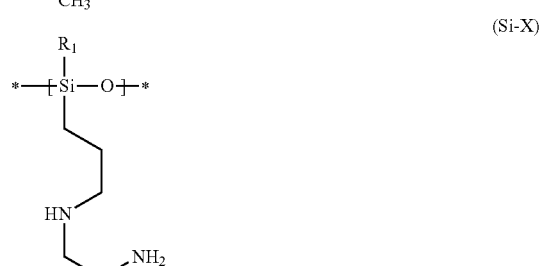
(Si-X)

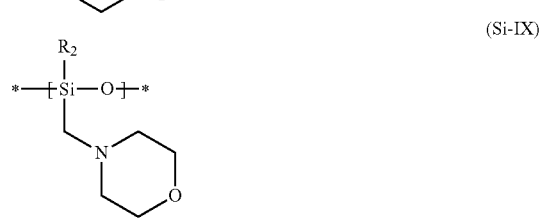
(Si-IX)

in which
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.

Particularly preferred compositions (a) as contemplated herein contain at least one 4-morpholinomethyl-substituted silicone of the formula (Si-XI)

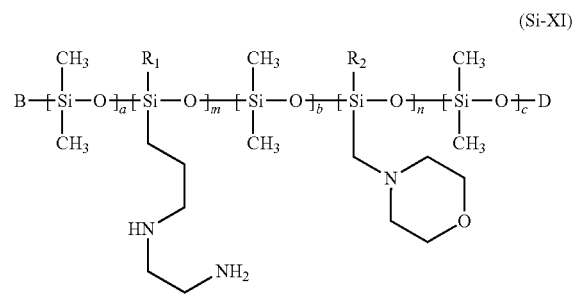
(Si-XI)

located in the
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
a, b and c stand independently for integers between 0 and 1000, with the condition a+b+c>0
m and n independently of each other stand for integers between 1 and 1000
with the proviso that at least one of the conditions B=—OH or D=—H is fulfilled, the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m and n are preferably statistically distributed.

The silicones used as contemplated herein represented by formula (Si-VI) can be trimethylsilyl-terminated (D or B=—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$OCH$_3$ and D=—Si(CH$_3$)$_2$OH to everyone. These silicones lead to exorbitant improvements in the hair properties of the hair treated with the agents of the present disclosure, and to a seriously improved protection in oxidative treatment.

It has been found to be particularly advantageous if the agent as contemplated herein includes the amino-functionalized silicone polymer(s) (a1) in certain quantity ranges. Particularly satisfactory results were obtained when the agent included—based on the total weight of the agent—a total amount of 0.1 to 8.0 wt. %, preferably 0.2 to 5.0 wt. %, more preferably 0.3 to 3.0 wt. %, and most preferably 0.4 to 2.5 wt. %.

In another particularly preferred embodiment, an agent as contemplated herein is wherein it includes—based on the total weight of the agent—one or more amino-functionalized silicone polymers (a1) in a total amount of from 0.1 to 8.0 wt. %, preferably from 0.2 to 5.0 wt. %, more preferably from 0.3 to 3.0 wt. % and very particularly preferably from 0.4 to 2.5 wt. %.

Coloring Compounds (a2)

As a second essential component, the composition as contemplated herein includes at least one color-imparting compound (a2).

For the purposes of the present disclosure, colorant compounds are substances capable of imparting a coloration to the keratin material. Particularly well-suited colorant compounds can be selected from the group of pigments, direct-acting dyes, photochromic dyes and thermochromic dyes.

In a further preferred embodiment, a composition as contemplated herein is wherein it includes at least one colorant compound (a2) from the group including pigments, direct dyes, photochromic dyes and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein is wherein it includes at least one colorant compound (a2) from the group including inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein is wherein it includes at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein is wherein it includes (a) at least one colorant compound (a2) from the group of pigments selected from mica- or mica-based pigments which are reacted with one or more metal oxides from the group including titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491(Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491(Iron oxides)
Colorona Blackstar Gold, Merck, MICA, CI 77499 (IRON OXIDES)

Other particularly preferred color pigments with the trade name Xirona® are for example:
Xirona Golden Sky, Merck, Silica, CI 77891 (Titanium Dioxide), Tin Oxide
Xirona Caribbean Blue, Merck, Mica, CI 77891 (Titanium Dioxide), Silica, Tin Oxide
Xirona Kiwi Rose, Merck, Silica, CI 77891 (Titanium Dioxide), Tin Oxide
Xirona Magic Mauve, Merck, Silica, CI 77891 (Titanium Dioxide), Tin Oxide.

In addition, particularly preferred color pigments with the trade name Unipure® are for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica In a further embodiment, the composition as contemplated herein may also include one or more colorant compounds (a2) selected from the group of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyorrole, indigo, thioindido, dioxazine and/or triarylmethane compounds.

Examples of particularly suitable organic pigments are carmine, quinacridone, phthalocyanine, sorghum, blue pigments with the Color Index numbers C1 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, an agent as contemplated herein is wherein it includes at least one colorant compound (a2) from the group of organic pigments which is preferably selected from the group of carmine, quinacridone, phthalocyanine, sorghum, blue pigments having the color index numbers C1 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles including a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature stability, the use of the above pigments in agent (a) is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, 14 to 30 µm. The mean particle size $D_{50}$, for example, can be determined using dynamic light scattering (DLS).

The colorant compounds (a2), the colorant compounds from the group of pigments, represent the second essential of the agent as contemplated herein and are preferably used in the agent in certain ranges of amounts.

Particularly satisfactory results were obtained when the agent included—based on the total weight of the agent—one or more pigments (a2) in a total amount of 0.01 to 10.0 wt. %, preferably 0.1 to 5.0 wt. %, further preferably 0.2 to 2.5 wt. % and very preferably 0.25 to 1.5 wt. %.

In another very particularly preferred embodiment, an agent as contemplated herein is wherein the agent includes—based on the total weight of the agent—one or more pigments (a2) in a total amount of from 0.01 to 10.0 wt. %, preferably from 0.1 to 5.0 wt. %, more preferably from 0.2 to 2.5 wt. % and very particularly preferably from 0.25 to 1.5 wt. %.

As colorant compounds (a2), the agent as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1.0 g/L.

Direct dyes can be divided into anionic, cationic and non-ionic direct dyes.

In a further embodiment, a process as contemplated herein is wherein the agent (a) includes at least one colorant compound (a2) from the group including anionic, non-ionic and cationic direct dyes.

Suitable cationic direct dyes include Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51 Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethyl-amino-4-nitrophenol.

Anionic direct dyes are also called acid dyes. Acid dyes are direct dyes that have at least one carboxylic acid group (—COOH) and/or one sulphonic acid group (—SO$_3$H). Depending on the pH value, the protonated forms (—COOH, —SO$_3$H) of the carboxylic acid or sulphonic acid groups are in equilibrium with their deprotonated forms (—COO$^-$, —SO$_3^-$ present). The proportion of protonated forms increases with decreasing pH. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

In another embodiment, a process for dyeing keratinous material is wherein the agent (a) includes at least one anionic direct dye selected from the group of nitrophenylenediamines, nitroaminophenols, azo dyes, anthraquinone dyes, triarylmethane dyes, xanthene dyes, rhodamine dyes, oxazine dyes and/or indophenol dyes, the rhodamine dyes, the oxazine dyes and/or the indophenol dyes, the dyes from the abovementioned group each having at least one carboxylic acid group (—COOH), a sodium carboxylate group (—COONa), a potassium carboxylate group (—COOK), a sulfonic acid group (—SO$_3$H), a sodium sulfonate group (—SO$_3$Na) and/or a potassium sulfonate group (—SO$_3$K).

Suitable acid dyes may include, for example, one or more compounds selected from the following group: Acid Yellow 1 (D&C Yellow 7, Citronin A, Ext. D&C Yellow No. 7, Japan Yellow 403, CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C015), Acid Orange 10 (C.I. 16230;

Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodium-salt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiod-fluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet n° 2, C.I. 60730, COLIPA n° C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-di-one and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has an extremely high water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)ben-zoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonato-benzyl)imino]-2,5-cyclohexadien-1-ylidene}methyl)-ben-zenesulfonate and has a solubility in water of more than 20 wt. % (25° C.).

In a further embodiment, an agent as contemplated herein is therefore wherein it includes at least one direct dye (a2) selected from the group of acid yellow 1, acid yellow 3, acid yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct-acting dye or dyes can be used in various amounts in the agents, depending on the desired color intensity. Satisfactory results were obtained when the agent includes—based on the total weight of the agent—one or more direct dyes (a2) in a total amount of from 0.01 to 10.0 wt. %, preferably from 0.1 to 8.0 wt. %, more preferably from 0.2 to 6.0 wt. % and most preferably from 0.5 to 4.5 wt. %.

Furthermore, the agent may also contain at least one photochromic or thermochromic dye as the coloring compound (a2).

Photochromic dyes are dyes that react to irradiation with UV light (sunlight or black light) with a reversible change in hue. In this process, the UV light changes the chemical structure of the dyes and thus their absorption behavior (photochromism).

Thermochromic dyes are dyes that react to temperature changes with a reversible change in hue. In this process, the change in temperature alters the chemical structure of the dyes and thus their absorption behavior (Thermochromism).

The agent may contain—based on the total weight of the composition—one or more photochromic dyes (a2) in a total amount of from 0.01 to 10.0 wt. %, preferably from 0.1 to 8.0 wt. %, more preferably from 0.2 to 6.0 wt. % and most preferably from 0.5 to 4.5 wt. %

Ethoxylated Fatty Acid Esters (a3)

As a third essential ingredient (a3), the agents as contemplated herein contain at least one addition product of ethylene oxide to the esters of $C_{12}$-$C_{24}$ fatty acids and $C_1$-$C_{12}$ aliphatic alcohols.

The addition products of ethylene oxide to the esters of $C_{12}$-$C_{24}$ fatty acids and $C_1$-$C_{12}$ aliphatic alcohols (a3) can also be briefly referred to as ethoxylated fatty acid esters (a3).

The ethoxylated fatty acid esters (a3) are based on $C_{12}$-$C_{24}$ fatty acids. These $C_{12}$-$C_{24}$ fatty acids as contemplated herein are linear or branched, saturated or mono- or polyunsaturated fatty acids, which may also bear one or more hydroxy groups. The $C_{12}$-$C_{24}$ fatty acids as contemplated herein are exemplified in which they contain 12 to 24 carbon atoms. Furthermore, the $C_{12}$-$C_{24}$-fatty acids carry at least one carboxylic acid group. This carboxylic acid moiety either forms an ester with the $C_1$-$C_{12}$ aliphatic alcohols, or forms an adduct with ethylene oxide, with this adduct then reacting further with a $C_1$-$C_{12}$ aliphatic alcohol.

To form the ethoxylated fatty acid esters (a3) as contemplated herein, for example, one or more fatty acids selected from the group of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselic acid [(Z)-6-octadecenoic acid], palmitoleic acid [(9Z)-hexadec-9-enoic acid], Oleic acid [(9Z)-Octadec-9-enoic acid], Elaidic acid [(9E)-Octadec-9-enoic acid], Erucic acid [(13Z)-Docos-13-enoic acid], Linoleic acid [(9Z,12Z)-Octadeca-9,12-dienoic acid, Linolenic acid [(9Z,12Z,15Z)-Octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], nervonic acid [(15Z)-tetracos-15-enoic acid] and/or castor oleic acid ((9Z,12R)-12-hydroxy-9-octadecenoic acid.

The ethoxylated fatty acid esters (a3) represent addition products of ethylene oxide to the esters of the previously described $C_{12}$-$C_{24}$ fatty acids and $C_1$-$C_{12}$ aliphatic alcohols. A characteristic feature of the $C_1$-$C_{12}$ alcohols is that they include 1 to 12 carbon atoms. The alcohols are aliphatic and can be linear or branched, saturated or mono- or polyunsaturated. The corresponding $C_1$-$C_{12}$ alcohols can be monohydric or polyhydric alcohols, i.e., the alcohols can have one or more hydroxyl groups.

Monovalent $C_1$-$C_{12}$ alcohols have a hydroxyl group. Suitable representatives may include methanol, ethanol, n-propanol, iso-propanol, n-butanol, n-pentanol, n-hexanol, n-octanol, n-decanol and n-dodecanol.

Bivalent $C_1$-$C_{12}$ alcohols have two hydroxyl groups. Suitable representatives may include, for example, 1,2-ethanediol, 1,2-propanediol, 1,3-propanediol, 1,4-butanediol, 1,5-pentanediol, 1,2-hexanediol, 1,6-hexanediol, 1,2-octanediol, 1,8-octanediol.

If bivalent $C_1$-$C_{12}$ alcohols are used to form the esters, one or both hydroxyl groups may form an ester group with the $C_{12}$-$C_{24}$ fatty acid(s).

One or more moles of ethylene oxide can also be attached to the free hydroxyl group.

Trivalent $C_1$-$C_{12}$ alcohols have three hydroxyl groups. Glycerin, for example, can be named as a suitable representative.

When trivalent $C_1$-$C_{12}$ alcohols are used to form the esters, one, both, and all three hydroxyl groups may form an ester group with the $C_{12}$-$C_{24}$ fatty acid(s).

One or more moles of ethylene oxide can also be attached to the free hydroxyl group(s).

A corresponding addition product of ethylene oxide to the esters of $C_{12}$-$C_{24}$ fatty acids and aliphatic $C_1$-$C_{12}$ alcohols (a3) is formed when the $C_{12}$-$C_{24}$ fatty acid itself or the ester already formed from it is reacted with ethylene oxide (alternatively 1,2-epoxyethane, CAS number 75-21-8).

If the $C_{12}$-$C_{24}$ fatty acid itself is rearranged with ethylene oxide, an adduct may initially form starting from the carboxylic acid moiety of the $C_{12}$-$C_{24}$ fatty acid and the ethylene oxide, resulting in a moiety *—C(O)—O—$CH_2$—$CH_2$—O—*. This grouping is also an ester. If one mole of ethylene oxide is reacted per mole of fatty acid, a simple adduct with one unit of *—$CH_2$—$CH_2$—O—* is formed on average. However, depending on the molar excess of ethylene oxide used, multiple adducts can also form, with several units of *—$CH_2$—$CH_2$—O—* present per mole of $C_{12}$-$C_{24}$ fatty acid. To form the ester (a3), this adduct can then be further reacted with at least one $C_1$-$C_{12}$ alcohol.

The positions marked with an asterisk here represent the bond to the remaining part of the fatty acid and the bond with the remaining part of the alcohol.

Formally, this type of addition products of ethylene oxide to the esters of $C_{12}$-$C_{24}$ fatty acids and aliphatic $C_1$-$C_{12}$ alcohols (a3) is thus represented in such a way that one or more units —O—$CH_2$—$CH_2$— are located between the carbonyl group of the fatty acid and the oxygen atom of the alcohol.

Another type of addition product of ethylene oxide to the esters of $C_{12}$-$C_{24}$ fatty acids and $C_1$-$C_{12}$ aliphatic alcohols (a3) is when an ester is reacted with ethylene oxide, said ester having been obtained by esterification of a $C_{12}$-$C_{14}$ fatty acid having at least one hydroxy group with a $C_1$-$C_{12}$ alcohol. For example, castor oleic acid ((9Z,12R)-12-hydroxy-9-octadecenoic acid) can first be esterified with methanol, ethanol or glycerol. When these adducts are formed, the ethylene oxide now attaches to the hydroxyl group of the castor oil acid and/or to the still free hydroxyl groups of the glycerol.

If one mole of ethylene oxide is reacted per mole of fatty acid, for example, one unit of *—$CH_2$—$CH_2$—O—* can be added to the hydroxyl group of castor oil acid. However, depending on the molar excess of ethylene oxide used, multiple adducts can also be formed, with several units of *—$CH_2$—$CH_2$—O—* added to each hydroxyl group of the fatty acid, and/or with several units of *—$CH_2$—$CH_2$—O—* also added to each free hydroxyl group of the glycerol.

The use of specific $C_1$-$C_{12}$ alcohols for the formation of the ethoxylated fatty acid ester (a3) has proved to be particularly suitable for solving the problem as contemplated herein. Particularly beneficial effects were observed when at least one addition product of ethylene oxide to an ester obtained by esterification of one, two or three $C_{12}$-$C_{24}$ fatty acids with glycerol was present.

In the context of a further very particularly preferred embodiment, an agent as contemplated herein is wherein it (a3) includes at least one addition product of ethylene oxide to an ester obtained by esterification of one, two or three $C_{12}$-$C_{24}$ fatty acids with glycerol.

A particularly suitable group of ethoxylated fatty acid esters (a3) is represented by compounds of the general formula (EFA-I).

In the context of a further very particularly preferred embodiment, an agent as contemplated herein is wherein it (a3) includes at least one ethoxylated fatty acid ester of the general formula (EFA-I)

(EFA-I)

where
R1, R2, R3 independently represent a grouping —($CH_2$—$CH_2$—O)$_v$—H, or a grouping of the general formula (EFA-II),

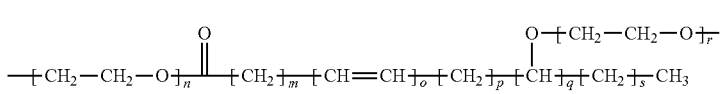
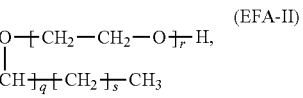

(EFA-II)

where
V represents an integer from 0 to 100,
n represents an integer from 0 to 100,
m represents an integer from 1 to 8,
represents an integer from 0 to 3,
P represents an integer from 1 to 8,
q represents the number 0 or 1,
r represents an integer from 1 to 100, and
s represents an integer from 1 to 8,
provided that
  at least one of the radicals R1, R2, R3 represents a grouping of the general formula (EFA-II), and in that
  at least one of the index numbers for v, n and/or q is a number not equal to 0.

The compounds of the formula (EFA-I) are based on the $C_1$-$C_{12}$ alcohol glycerol, which carries the radicals R1, R2 and R3.

The radicals R1, R2 and R3 can be selected independently of each other. The substituents in the radicals R1, R2, and R3 can also each be chosen independently.

R1, R2, R3 independently represent a grouping —($CH_2$—$CH_2$—O)$_v$—H, or a grouping of the general formula (EFA-II).

The index number v can stand for an integer from 0 to 100.

Here, the requirement is that at least one of the radicals R1, R2, R3 represents a grouping of the general formula (EFA-II).

Since at least one of the radicals R1, R2, R3 represents a grouping of the general formula (EFA-II), it is guaranteed that the compound of formula (EFA-I) is in the form of an ester of glycerol and a $C_{12}$-$C_{24}$ fatty acid.

Furthermore, there is the requirement that at least one of the index numbers for v, n and/or q stands for a number not equal to 0.

If only the radical R1 represents a compound of the formula (EFA-II), then the other two radicals R2, and R3 each independently represent a grouping —($CH_2$—$CH_2$—O)$_v$—H.

In each of the two radicals R2 and R3, the index number v can be chosen independently of the other radical. The provision that at least one index number v, n and/or q is a number other than 0 ensures that the compound of the formula (EFA-I) is in the form of an ethoxylated fatty acid ester.

If two radicals from R1, R2, and R3 stand for a compound of formula (EFA-II), then the remaining radical stands for a The provision that at least one index number v, n and/or q is a number other than 0 ensures that the compound of the formula (EFA-I) is in the form of an ethoxylated fatty acid ester.

If all three radicals R1, R2, and R3 represent a compound of the formula (EFA-II), then of course none of these radicals can represent a grouping —($CH_2$—$CH_2$—O)$_v$—H. In each of the formulas (EFA-II), the index numbers can be selected independently of the index numbers of the other formula (EFA-II). In this case there is no index number v. Also, in case the condition applies that at least one index number v, n and/or q stands for a number not equal to 0. However, since the index number v does not exist in the context of this embodiment, this means that at least one of the existing index numbers n and/or q must stand for a number not equal to 0.

By specifying that at least one of the index numbers v, n and/or q is a number other than 0, it is ensured that at least one adduct with ethylene oxide is present in the compound of the formula (EFA-I), so that at least one grouping *—$CH_2$—$CH_2$—O—* is present in the molecule.

The index numbers n, m, o, p, q, r, and s can be selected in each structural unit of the formula (EFA-II) independently of the other structural units.

The index number n stands for an integer from 0 to 100.
The index number r stands for an integer from 1 to 100.
The numbers n and r indicate the number of ethylene oxide units in each structural unit of the formula (EFA-II).
The index number m stands for an integer from 1 to 8.
The index number o stands for an integer from 0 to 3.
The index number p stands for an integer from 1 to 8.
The index number q stands for the number 0 or 1.
The index number s stands for an integer from 1 to 8.
The index numbers m, o, p, q and s define the length of the $C_{12}$-$C_{24}$ fatty acid. Here, too, the requirement must be met that all index numbers are chosen so that the structural unit of the formula (EFA-II) is derived from a $C_{12}$-$C_{24}$ fatty acid.

Colorations with particularly high color intensity were obtained when an agent as contemplated herein including at least one ethoxylated fatty acid ester (a3) of the general formula (EFA-I) was applied to the keratin material, where
R1, R2, R3 independently represent a grouping of the general formula (EFA-II),

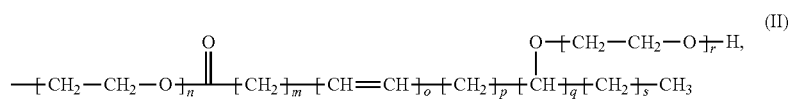

(II)

grouping —($CH_2$—$CH_2$—O)$_v$—H. In each of the formulas (EFA-II), the index numbers can be chosen independently of the index numbers of the other formula (EFA-II). The remaining radical from R1, R2 and R3 represents the grouping —($CH_2$—$CH_2$—O)$_v$—H.

where
n represents the number of 0
m represents an integer from 1 to 8,
represents the number 0 or 1, preferably the number 0,
P represents an integer from 1 to 8, q represents the number 1,
r represents an integer from 1 to 100, and
s represents an integer from 1 to 8.

In the context of a further very particularly preferred embodiment, an agent as contemplated herein is wherein it (a3) includes at least one ethoxylated fatty acid ester of the general formula (EFA-I)
where
R1, R2, R3 independently represent a grouping of the general formula (EFA-II),

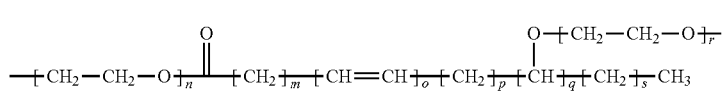

where
n represents the number of 0
m represents an integer from 1 to 8,
represents the number 0 or 1, preferably the number 0,
P represents an integer from 1 to 8,
q represents the number 1,
r represents an integer from 1 to 100, and
s represents an integer from 1 to 8.

The index numbers m, o, p, q and s again define the length of the $C_{12}$-$C_{24}$ fatty acid, again with the proviso that all index numbers are chosen so that the structural unit of the formula (EFA-II) is derived from a $C_{12}$-$C_{24}$ fatty acid.

If o stands for the number 0, the sum of m, p, q and s is an integer from 10 to 22. If o stands for the number 1, the sum of m, p, q and s is an integer from 8 to 20.

The ethoxylated fatty acid esters (a3) selected from the group of PEG-5 Hydrogenated Castor Oil, PEG-10 Hydrogenated Castor Oil, PEG-20 Hydrogenated Castor Oil, PEG-30 Hydrogenated Castor Oil, PEG-40 Hydrogenated Castor Oil, PEG-50 Hydrogenated Castor Oil, PEG-60 Hydrogenated Castor Oil, PEG-70 Hydrogenated Castor Oil, PEG-80 Hydrogenated Castor Oil, PEG-90 Hydrogenated Castor Oil, PEG-100 Hydrogenated Castor Oil, PEG-5 Castor Oil, PEG-10 Castor Oil, PEG-20 Castor Oil, PEG-30 Castor Oil, PEG-40 Castor Oil, PEG-50 Castor Oil, PEG-60 Castor Oil, PEG-70 Castor Oil, PEG-70 Castor Oil, PEG-80 Castor Oil, PEG-90 Castor Oil and PEG-100 Castor Oil.

In the context of a further very particularly preferred embodiment, an agent as contemplated herein is wherein it (a3) includes at least one ethoxylated fatty acid ester selected from the group of PEG-5 Hydrogenated Castor Oil, PEG-10 Hydrogenated Castor Oil, PEG-20 Hydrogenated Castor Oil, PEG-30 Hydrogenated Castor Oil, PEG-40 Hydrogenated Castor Oil, PEG-50 Hydrogenated Castor Oil, PEG-60 Hydrogenated Castor Oil, PEG-70 Hydrogenated Castor Oil, PEG-80 Hydrogenated Castor Oil, PEG-90 Hydrogenated Castor Oil, PEG-100 Hydrogenated Castor Oil, PEG-5 Castor Oil, PEG-10 Castor Oil, PEG-20 Castor Oil, PEG-30 castor oil, PEG-40 castor oil, PEG-50 castor oil, PEG-60 castor oil, PEG-70 castor oil, PEG-70 castor oil, PEG-80 castor oil, PEG-90 castor oil and PEG-100 castor oil.

The most preferred is PEG-60 Hydrogenated Castor Oil (a3).

PEG-60 Hydrogenated Castor Oil carries the CAS number 61788-85-0 and may alternatively be referred to as Castor oil, hydrogenated, ethoxylated (60 EO). It can be purchased commercially under the trade name Eumulgin CO 60 from BASF, for example.

In another embodiment, the ethoxylated fatty alcohols of general formula (EFA-I) (a3) have proved to be particularly suitable, where
R1, R2, R3 independently of one another represent a hydrogen atom, a grouping —($CH_2$—$CH_2$—O$)_v$—H, or a grouping of the general formula (EFA-II),

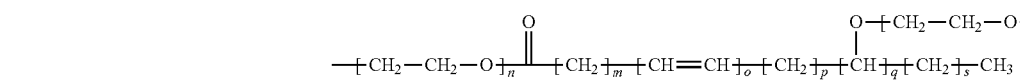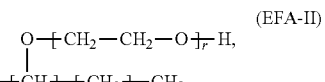

where
V represents an integer from 0 to 100,
n is an integer from 0 to 100, preferably an integer from 1 to 10
m represents an integer from 1 to 8,
represents the number 0,
P represents an integer from 1 to 8,
q represents the number 0,
s represents an integer from 1 to 8,
provided that
at least one of the radicals R1, R2, R3 represents a grouping of the general formula (II), and in that
at least one of the index numbers for v and/or n is a number not equal to 0.

In the context of a further very particularly preferred embodiment, an agent as contemplated herein is wherein it (a3) includes at least one ethoxylated fatty acid ester of the general formula (EFA-I)
where
R1, R2, R3 independently of one another represent a hydrogen atom, a grouping —($CH_2$—$CH_2$—O$)_v$—H, or a grouping of the general formula (EFA-II),

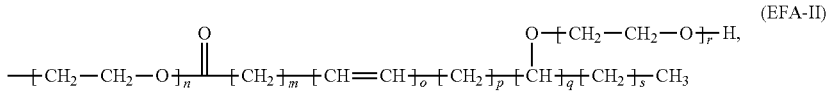
(EFA-II)

where
V represents an integer from 0 to 100,
n is an integer from 0 to 100, preferably an integer from 1 to 10
m represents an integer from 1 to 8,
represents the number 0,
p represents an integer from 1 to 8,
q represents the number 0,
s represents an integer from 1 to 8,
provided that
  at least one of the radicals R1, R2, R3 represents a grouping of the general formula (II), and in that
  at least one of the index numbers for v and/or n is a number not equal to 0.

If only the radical R1 represents a compound of the formula (EFA-II), then the other two radicals R2, and R3 each independently represent a grouping —$(CH_2—CH_2—O)_v$—H.

In each of the two radicals R2 and R3, the index number v can be chosen independently of the other radical. Since the index number q stands for 0, no grouping exists which carries the index number r. The provision that at least one index number v and/or n is a number other than 0 ensures that the compound of the formula (EFA-I) is in the form of an ethoxylated fatty acid ester.

If two radicals from R1, R2, and R3 stand for a compound of formula (EFA-II), then the remaining radical stands for a grouping —$(CH_2—CH_2—O)_v$—H. In each of the formulas (EFA-II), the index numbers can be chosen independently of the index numbers of the other formula (EFA-II). The remaining radical from R1, R2 and R3 represents the grouping —$(CH_2—CH_2—O)_v$—H.

Since the index number q stands for 0, no grouping exists which carries the index number r. The provision that at least one index number v and/or n is a number other than 0 ensures that the compound of the formula (EFA-I) is in the form of an ethoxylated fatty acid ester.

If all three radicals R1, R2, and R3 represent a compound of the formula (EFA-II), then of course none of these radicals can represent a grouping —$(CH_2—CH_2—O)_v$—H. In each of the formulas (EFA-II), the index numbers can be selected independently of the index numbers of the other formula (EFA-II). In this case, there is no index number v. Since the index number q stands for 0, there is also no grouping that carries the index number r. Also, in case the condition applies that at least one index number v and/or n stands for a number not equal to 0. However, since the index number v does not exist in the context of this embodiment, this means that at least one of the existing index numbers n must stand for a number other than 0.

The index number v stands for an integer from 0 to 100.

In the context of this embodiment, n represents an integer from 0 to 100, preferably n represents an integer from 0 to 10. The index number q stands for the number 0.
The number of units *—$CH_2$—$CH_2$—O—* in each structural unit (EFA-II) is therefore given by the respective index number n.

The index numbers o and q both stand for the number 0. Thus, the length of the $C_{12}$-$C_{24}$ fatty acid is defined by the index numbers m, p, and s, again with the requirement that all index numbers are chosen such that the structural unit of the formula (EFA-II) is derived from a $C_{12}$-$C_{24}$ fatty acid.

Here, the sum of m, p, and s is an integer from 10 to 22.

Furthermore, the ethoxylated fatty acid esters (a3) selected from the group of PEG-7 glyceryl monolaurate, PEG-7 glyceryl monomyristate, PEG-7 glyceryl monopalmitate, PEG-7 glyceryl monostearate, PEG-7 glyceryl monocaprylate, PEG-7 glyceryl monocaprate, PEG-10 glyceryl monolaurate, PEG-10 glyceryl monomyristate, PEG-10 glyceryl monopalmitate, PEG-10 glyceryl monostearate, PEG-10 glyceryl monocaprylate, PEG-10 glyceryl monocaprate, PEG-5 glyceryl monolaurate, PEG-5 glyceryl monomyristate, PEG-5 glyceryl monopalmitate, PEG-5 glyceryl monostearate, PEG-5 glyceryl monocaprylate, PEG-5 glyceryl monocaprate, PEG-7 glyceryl cocoate, PEG-7 glyceryl dilaurate, PEG-7 glyceryl dimyristate, PEG-7 glyceryl dipalmitate, PEG-7 glyceryl distearate, PEG-7 glyceryl dicaprylate, PEG-7 glyceryl dicaprate, PEG-10 glyceryl dilaurate, PEG-10 glyceryl dimyristate, PEG-10 glyceryl dipalmitate, PEG-10 glyceryl distearate, PEG-10 glyceryl dicaprylate, PEG-10 glyceryl dicaprate, PEG-5 glyceryl dilaurate, PEG-5 glyceryl dimyristate, PEG-5 glyceryl dipalmitate, PEG-5 glyceryl distearate, PEG-5 glyceryl dicaprylate, PEG-5 glyceryl dicaprate, PEG-7 glyceryl cocoate, PEG-7 glyceryl trilaurate, PEG-7 glyceryl trimyristate, PEG-7 glyceryl tripalmitate, PEG-7 glyceryl tristearate, PEG-7 glyceryl tricaprylate, PEG-7 glyceryl tricaprate, PEG-10 glyceryl trilaurate, PEG-10 glyceryl trimyristate, PEG-10 glyceryl tripalmitate, PEG-10 glyceryl tristearate, PEG-10 glyceryl tricaprylate, PEG-10 glyceryl tricaprate, PEG-5 glyceryl trilaurate, PEG-5 glyceryl trimyristate, PEG-5 glyceryl tripalmitate, PEG-5 glyceryl tristearate, PEG-5 glyceryl tricaprylate, PEG-5 glyceryl tricaprate, PEG-7 glyceryl cocoate and mixtures thereof.

In the context of a further very particularly preferred embodiment, an agent as contemplated herein is wherein it (a3) includes at least one ethoxylated fatty acid ester selected from the group of PEG-7 glyceryl monolaurate, PEG-7 glyceryl monomyristate, PEG-7 glyceryl monopalmitate, PEG-7 glyceryl monostearate, PEG-7 glyceryl monocaprylate, PEG-7 glyceryl monocaprate, PEG-10 glyceryl monolaurate, PEG-10 glyceryl monomyristate, PEG-10 glyceryl monopalmitate, PEG-10 glyceryl monostearate, PEG-10 glyceryl monocaprylate, PEG-10 glyceryl monocaprate, PEG-5 glyceryl monolaurate, PEG-5 glyceryl monomyristate, PEG-5 glyceryl monopalmitate, PEG-5 glyceryl monostearate, PEG-5 glyceryl monocaprylate, PEG-5 glyceryl monocaprate, PEG-7 glyceryl cocoate, PEG-7 glyceryl dilaurate, PEG-7 glyceryl dimyristate, PEG-7 glyceryl dipalmitate, PEG-7 glyceryl distearate, PEG-7 glyceryl dicaprylate, PEG-7 glyceryl dicaprate, PEG-10 glyceryl dilaurate, PEG-10 glyceryl dimyristate, PEG-10 glyceryl dipalmitate, PEG-10 glyceryl distearate, PEG-10 glyceryl dicaprylate, PEG-10 glyceryl dicaprate, PEG-5 glyceryl dilaurate, PEG-5 glyceryl dimyristate, PEG-5 glyceryl dipalmitate, PEG-5 glyceryl distearate, PEG-5 glyceryl dicaprylate, PEG-5 glyceryl dicaprate, PEG-7 glyceryl cocoate, PEG-7 glyceryl trilaurate, PEG-7 glyceryl trimyristate, PEG-7 glyceryl tripalmitate, PEG-7 glyceryl tristearate, PEG-7 glyceryl tricaprylate, PEG-7 glyceryl tricaprate, PEG-10 glyceryl trilaurate, PEG-10 glyceryl trimyristate, PEG-10 glyceryl tripalmitate, PEG-10 glyceryl tristearate, PEG-10 glyceryl tricaprylate, PEG-10 glyceryl tricaprate, PEG-5 glyceryl trilaurate, PEG-5 glyceryl trimyristate, PEG-5 glyceryl tripalmitate, PEG-5 glyceryl tristearate, PEG-5 glyceryl tricaprylate, PEG-5 glyceryl tricaprate, PEG-7 glyceryl cocoate and mixtures thereof.

Explicitly preferred is PEG-7 Glyceryl Cocoate, which has the CAS number 68553-02-6 and can be purchased commercially, for example, under the trade name Cetiol HE from BASF.

The ethoxylated fatty acid esters (a3) are particularly preferred in certain ranges of amounts in the agent as contemplated herein.

Particularly satisfactory results were obtained when the agent included—based on the total weight of the composition—one or more ethoxylated fatty acid esters (a3) in a total amount of from 0.1 to 20.0 wt. %, preferably from 0.5 to 15.0 wt. %, more preferably from 1.0 to 10.0 wt. % and most preferably from 4.0 to 8.0 wt. %.

In a further preferred embodiment, an agent as contemplated herein is wherein it includes—based on the total weight of the composition—one or more ethoxylated fatty acid esters (a3) in a total amount of from 0.1 to 20.0 wt. %, preferably from 0.5 to 15.0 wt. %, more preferably from 1.0 to 10.0 wt. % and very particularly preferably from 4.0 to 8.0 wt. %.

Fat Components in Agent

As a further optional ingredient, the agent as contemplated herein may also additionally include at least one fat ingredient.

It has been found that the use of at least one fat component results in the agent being in the form of an emulsion, which has the optimum viscosity and has also been found to be beneficial in terms of improving color intensity.

The fatty components are hydrophobic substances that can form emulsions in the presence of water, forming micelle systems.

For the purposes of the present disclosure, "fatty components" means organic compounds with a solubility in water at room temperature (22° C.) and atmospheric pressure (760 mmHg) of less than 1 wt. %, preferably less than 0.1 wt. %. The definition of fat constituents explicitly covers only uncharged (i.e., non-ionic) compounds. Fat components have at least one saturated or unsaturated alkyl group with at least 12 C atoms. The molecular weight of the fat constituents is a maximum of 5000 g/mol, preferably a maximum of 2500 g/mol and particularly preferably a maximum of 1000 g/mol. The fat components are neither ethoxylated, nor polyoxyalkylated, nor polyglycerylated compounds.

Very preferably, the fat constituents (a4) included in the composition are selected from the group of $C_{12}$-$C_{24}$ fatty alcohols, $C_{12}$-$C_{24}$ fatty acid triglycerides, $C_{12}$-$C_{24}$ fatty acid monoglycerides, $C_{12}$-$C_{24}$ fatty acid diglycerides and/or hydrocarbons.

In the context of a further preferred embodiment, an agent as contemplated herein is wherein it includes one or more fat constituents from the group including the $C_{12}$-$C_{24}$ fatty alcohols, the $C_{12}$-$C_{24}$ fatty acid triglycerides, the $C_{12}$-$C_{24}$ fatty acid monoglycerides, the $C_{12}$-$C_{24}$ fatty acid diglycerides and/or the hydrocarbons.

In this context, very particularly preferred fat constituents are understood to be constituents from the group of $C_{12}$-$C_{24}$ fatty alcohols, $C_{12}$-$C_{24}$ fatty acid triglycerides, $C_{12}$-$C_{24}$ fatty acid monoglycerides, $C_{12}$-$C_{24}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{24}$ fatty alcohols can be saturated, mono- or polyunsaturated, linear or branched fatty alcohols with 12 to 24 C atoms.

Examples of preferred linear, saturated $C_{12}$-$C_{24}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z, 11Z, 14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol.

In another preferred embodiment, an agent as contemplated herein is wherein it includes one or more $C_{12}$-$C_{24}$ fatty alcohols selected from the group of.

Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol includes.

It has been found to be quite preferable to use one or more $C_{12}$-$C_{24}$ fatty alcohols in quite specific ranges of amounts.

It is particularly preferred if the agent includes one or more $C_{12}$-$C_{24}$ fatty alcohols in a total amount—based on the total weight of the composition—of from 2.0 to 50.0 wt. %, preferably from 3.0 to 30.0 wt. %, more preferably from 4.0 to 20.0 wt. %, still more preferably from 5.0 to 15.0 wt. %, and most preferably from 5.0 to 10.0 wt. %.

Further, as a suitable fat ingredient, the agent may also contain at least one $C_{12}$-$C_{24}$ fatty acid triglyceride that is $C_{12}$-$C_{24}$ fatty acid monoglyceride and/or $C_{12}$-$C_{24}$ fatty acid diglyceride. For the purposes of the present disclosure, a $C_{12}$-$C_{24}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched or branched, unsubstituted or substituted $C_{12}$-$C_{24}$ carboxylic acids. Unsaturated fatty acids can be mono- or polyunsaturated. For an unsaturated fatty acid, its C=C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{24}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{24}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{24}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z,12Z)-octadeca-9,12-dienoic acid], linolenic acid [(9Z,12Z,15Z)-octadeca-9,12,15-trienoic acid], elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when the agent included at least one $C_{12}$-$C_{24}$-fatty acid monoglyceride selected from the monoesters of glycerol with one equivalent of fatty acid from the group including dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselic acid [(Z)-6-octadecenoic acid], Palmitoleic acid [(9Z)-Hexadec-9-enoic acid], Oleic acid [(9Z)-Octadec-9-enoic acid], Elaidic acid [(9E)-Octadec-9-enoic acid], Erucic acid [(13Z)-Docos-13-enoic acid], Linoleic acid [(9Z,12Z)-Octadeca-9, 12-dienoic acid], linolenic acid [(9Z,12Z,15Z)-octadeca-9,12,15-trienoic acid, elaeostearic acid [(9Z,11E, 13E)-octadeca-9,11,3-trienoic acid], arachidonic acid [(5Z, 8Z,11Z,14Z)-icosa-5,8,11,14-tetraenoic acid] and/or nervonic acid [(15Z)-tetracos-15-enoic acid].

In the context of a further embodiment, an agent as contemplated herein is wherein it includes at least one $C_{12}$-$C_{24}$ fatty acid monoglyceride selected from the monoesters of glycerol with one equivalent of fatty acid from the group including dodecanoic acid, tetradecanoic acid, hexadecanoic acid, tetracosanoic acid, octadecanoic acid, eicosanoic acid and/or docosanoic acid.

It has been found preferable to use one or more $C_{12}$-$C_{24}$ fatty acid mono-, $C_{12}$-$C_{24}$-fatty acid di- and/or $C_{12}$-$C_{24}$ fatty acid triglycerides in specific ranges of amounts in the agent.

With regard to the solution of the task as contemplated herein, it has proved advantageous if the agent—based on the total weight of the agent—included one or more $C_{12}$-$C_{24}$ fatty acid mono-, $C_{12}$-$C_{24}$ fatty acid di- and/or $C_{12}$-$C_{24}$ fatty acid triglycerides in a total amount of 0.1 to 20.0 wt. %, preferably from 0.3 to 15.0 wt. %, more preferably from 0.5 to 10.0 wt. %, and most preferably from 0.8 to 5.0 wt. %.

Furthermore, as a very particularly preferred fat constituent, the agents may also contain at least one hydrocarbon.

Hydrocarbons are compounds including exclusively the atoms carbon and hydrogen with 8 to 80 C atoms. In this context, aliphatic hydrocarbons such as mineral oils, liquid paraffin oils (e.g., Paraffinum Liquidum or Paraffinum Perliquidum), isoparaffin oils, semi-solid paraffin oils, paraffin waxes, hard paraffin (Paraffinum Solidum), Vaseline and polydecenes are particularly preferred.

Liquid paraffin oils (Paraffinum Liquidum and Paraffinum Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, including hydrocarbon chains with a C-chain distribution of 25 to 35 C-atoms.

Particularly satisfactory results were obtained when the agent included at least one hydrocarbon selected from the group of mineral oils, liquid kerosene oils, isoparaffin oils, semisolid kerosene oils, kerosene waxes, hard kerosene (Paraffinum solidum), petrolatum and polydecenes.

In a very particularly preferred embodiment, an agent as contemplated herein is wherein it includes at least one fatty constituent from the group of hydrocarbons.

Regarding the solution of the problem as contemplated herein, it proved to be quite particularly preferable if the agent included—based on the total weight of the composition—one or more hydrocarbons in a total amount of from 0.5 to 20.0 wt. %, preferably from 0.7 to 10.0 wt. %, more preferably from 0.9 to 5.0 wt. % and very particularly preferably from 1.0 to 4.0 wt. %.

In a very particularly preferred embodiment, an agent as contemplated herein is wherein it includes—based on the total weight of the agent—one or more hydrocarbons in a total amount of in a total amount of from 0.5 to 20.0 wt. %, preferably from 0.7 to 10.0 wt. %, more preferably from 0.9 to 5.0 wt. % and very particularly preferably from 1.0 to 4.0 wt. %.

The hydrocarbon(s) may be used as the sole fatty ingredients (a4) in the compositions. However, it is also as contemplated herein to incorporate at least one hydrocarbon in combination with at least one other constituent into the agents.

Water Content in Agent

The agent described above is a ready-to-use agent that can be applied to the keratinous material. This ready-to-use agent preferably has a high water content. It has been found that particularly suitable agents are those including—based on the total weight of the agent—50.0 to 98.0 wt. %, preferably 60.0 to 90.0 wt. %, more preferably 70.0 to 90.0 wt. % and most preferably 75.0 to 90.0 wt. % of water.

In a further explicitly quite particularly preferred embodiment, an agent as contemplated herein is wherein it includes—based on the total weight of the agent—50.0 to 98.0 wt. %, preferably 60.0 to 90.0 wt. %, further preferably 70.0 to 90.0 wt. % and very particularly preferably 75.0 to 90.0 wt. % of water.

Other Optional Ingredients in the Agent

In addition to the ingredients (a1) to (a3) essential to the present disclosure already described, the agent may also contain further optional ingredients.

For example, the agent may contain a film-forming polymer. The film-forming polymer may be selected, for example, from the group including polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters or amides of (meth) acrylic acid having at least one $C_1$-$C_{20}$ alkyl group, an aryl group or a $C_2$-$C_{10}$ hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate); isobutyl (meth)acrylate; ethyl (meth)acrylate; methyl (meth) acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in those with $C_2$-$C_{18}$ alkyl groups, such as N-ethyl-acrylamide, N-tert-butyl-acrylamide, le N-octyl-crylamide; N-di($C_1$-$C_4$)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/ Steareth-20 Me-thacrylate Copolymer), Aculyn® 28 (Acrylate/Beheneth-25 Methacrylate Copolymer), Structure 2001® (Acryla-tes/Steareth-20 Itaconate Copolymer), Structure 3001® (Acrylate/Ceteth-20 Itaconate Copolymer), Structure Plus® (acrylate/aminoacrylate $C_{10}$-30 alkyl PEG-20 itaconate copolymer), Carbopol® 1342, 1382, Ultrez 20, Ultrez 21 (acrylate/$C_{10}$-30 alkyl acrylate crosspolymer), Synthalen W 2000® (acrylate/palmeth-25 acrylate copolymer) or Soltex OPT (acrylate/$C_{12}$-22 alkyl methacrylate copolymer) distributed by Rohme and Haas.

The homo- and copolymers of N-vinylpyrrolidone, vinylcaprolactam, vinyl-($C_1$-$C_6$)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHOMER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another version, block copolymers can be used as film-forming hydrophobic polymers, which include at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

If, in principle, both anionic and cationic and/or non-ionic polymers can be used in the agent as contemplated herein, it has proved particularly preferable not to use further ionic compounds or to use them only in insignificant amounts. In other words, a particularly strong improvement in color intensity could be achieved when the agent was a non-ionic base and therefore included cationic and anionic polymers either not at all or only in lesser amounts. For this reason, it has been found to be particularly preferable if the total content of all anionic polymers included in the agent is below 0.1 wt. %. Furthermore, it has been found to be particularly preferred if the total content of all cationic polymers included in the agent is below 0.1 wt. %. The amount of catalytic or anionic polymer is related to the total weight of the agent.

In another very particularly preferred embodiment, an agent as contemplated herein is wherein—in relation to the total weight of the means
the total content of all anionic polymers included in the agent is below 0.1 wt. %, and
the total content of all cationic polymers included in the agent is below 0.1 wt. %.

In addition to the non-ionic surfactants described above, the agents can in principle also contain one or more charged surfactants. The term surfactants refer to surface-active substances. A distinction is made between anionic surfactants including a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —COO$^{(-)}$— or —SO$_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —SO$_3$H group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino-propionates, aminoglycinate, imidazoliniumbetaines and sulfobetaines.

Examples of ampholytic surfactants are N-cocosalkylaminopropionate, cocosacylaminoethylaminopropionate and $C_{12}$-$C_{18}$-acyl sarcosine.

In addition, the agents may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually including a hydrocarbon backbone (e.g., including one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms,
quaternary phosphonium salts substituted with one or more alkyl chains with a chain length of 8 to 28 C atoms or
tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of 0.1 to 45 wt. %, preferably 1 to 30 wt. % and most preferably 1 to 15 wt. %—based on the total weight of the respective agent.

Furthermore, the agent as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

If, in principle, both anionic and cationic and/or non-ionic surfactants can be used in the agent as contemplated herein, it has proved particularly preferable not to use further ionic compounds or to use them only in small quantities. In other words, a particularly strong improvement in color intensity could be achieved when the agent was a non-ionic base and therefore included cationic and anionic surfactants either not at all or only in lesser amounts. For this reason, it has been found to be particularly preferable if the total content of all anionic surfactants included in the agent is below 0.1 wt. %. Furthermore, it has been found to be particularly preferable if the total content of all cationic surfactants included in the agent is below 0.1 wt. %. The amount of catalytic or anionic surfactant is related to the total weight of the product.

In another very particularly preferred embodiment, an agent as contemplated herein is wherein—in relation to the total weight of the means
the total content of all anionic surfactants included in the agent is below 0.1 wt. %, and
the total content of all cationic surfactants included in the agent is below 0.1 wt. %.

The agents may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxy cinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosene; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Agent pH Value

The pH value of the agent as contemplated herein is preferably adjusted to a neutral to alkaline pH. Most preferably, the agent has an alkaline pH value in the range of 7.0 to 11.5 preferably from 8.0 to 11.0, and most preferably from 8.5 to 10.5. Under basic conditions, the amino-functionalized silicone polymer (a1) can be dissolved or dispersed particularly well and without protonation.

Within the scope of a further preferred embodiment, an agent as contemplated herein is wherein it has a pH of from 7.0 to 11.5 preferably from 8.0 to 11.0, and particularly preferably from 8.5 to 10.5.

To adjust the desired pH, the agent (a) and/or (b) may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore wherein the agent as contemplated herein includes an alkanolamine selected from 2-aminoethan-1-ol and/or 2-amino-2-methylpropan-1-ol as alkalizing agent.

For the purposes of the present disclosure, an amino acid is an organic compound including at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore wherein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is wherein the colorant (a) includes at least one alkalizing agent selected from the group of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1, 3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Process for Dyeing Keratin Material

The agents described above can be excellently used in processes for dyeing keratinous material, especially human hair.

A second object of the present disclosure is therefore a method for coloring keratinous material, in particular human hair, including the following steps:

(1) Application of a coloring agent to the keratinous material, wherein the coloring agent is an agent as disclosed in detail in the description of the first subject matter of the present disclosure,
(2) Exposure of the colorant to the keratinous material and
(3) Rinse out the dye with water.

In step (1) of the process as contemplated herein, the agent of the first present disclosure is applied to the keratinous material, which is most preferably human hair.

In step (2) of the process as contemplated herein, the agent is then allowed to act on the keratinous material after its application. In this context, different exposure times of, for example, 30 seconds to 60 minutes are conceivable.

However, a major advantage of the dyeing system as contemplated herein is that an intensive color result can be achieved even in short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein is.
exemplified by:
(2) Exposure of the colorant to the keratinous material for a period ranging from 30 seconds to 15 minutes, preferably from 30 seconds to 10 minutes, and most preferably from 1 to 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the convenience of use, it has proved particularly preferable to rinse the agent in step (3) exclusively with water without the aid of a further after-treatment agent, shampoo or conditioner.

In a further preferred embodiment, a method as contemplated herein is.
exemplified by:
(3) Rinse out the dye with water only.

Concerning the further preferred embodiments of the method as contemplated herein, mutatis mutantis what has been said about the agents as contemplated herein applies.

Examples

1. Formulations

The following formulations were prepared (all data in wt. % unless otherwise stated):

| Colorants | (V1) | (E1) | (E2) |
|---|---|---|---|
| Cetyl alcohol | 6.0 | 6.0 | 6.0 |
| $C_{12}$-$C_{18}$-fatty alcohols (Lorol techn.) | 6.0 | 6.0 | 6.0 |
| Ceteareth-30 (Cetearyl alcohol, ethoxylated 30 EO) | 6.0 | — | — |
| PEG-7 glycerin coconut oil | — | 6.0 | — |
| PEG-60 Hydrogenated Castor Oil | — | — | 6.0 |
| Lavanya Zuni (organic pigment, Neelikon Red, 111P0200, CI 12490) | 1.0 | 1.0 | 1.0 |
| Dow Corning 2-8566 (Siloxanes and Silicones, 3-[(2-Aminoethyl)amino]-2-methylpropyl Me, Di-Me-Siloxane" | 2.5 | 2.5 | 2.5 |
| Ammonia (25% aqueous solution) | 0.20 | 0.20 | 0.20 |
| Water | ad 100 | ad 100 | ad 100 |

2. Application

After preparation, the respective agent (V1, E1 and E2) was applied to hair strands (Kerling, Euronatural hair white, liquor ratio: 1 g agent (E1) per g hair strand). The agent was left to act for three minutes. Subsequently, the hair strand was thoroughly washed (1 minute) with water, dried and then calorimetrically measured with a colorimeter from Datacolor, type Spectraflash 450.

The dE value used to assess the color intensity is derived from the L*a*b* colorimetric values measured on the respective strand part as follows:

$$dE=[(L_i-L_0)^2+(a_i-a_0)^2+(b_i-b_0)]^{1/2}$$

$L_0$, $a_0$ and $b_0$=Measured values of the comparative staining (V1)

$L_i$, $a_i$ ad $b_i$=Measured values of the dyeing as contemplated herein (E)

The chroma of a coloration is calculated according to the formula $$C=\sqrt{a^2+b^2}$$

The larger the C-value, the higher the chromaticity of a coloration.

The L-value indicates the brightness of a coloration. The lower the L-value is, the darker and more intense the coloration is

| Agent | L | a | b | Chroma C | dE for comparison |
|---|---|---|---|---|---|
| Comparison (V1) | 40.55 | 37.65 | 8.22 | 38.54 | |
| Invention (E1) | 28.96 | 47.52 | 18.02 | 50.82 | 18.10 |
| Invention (E2) | 29.18 | 45.76 | 15.19 | 48.21 | 15.61 |

Darker, more intense colorations (lower L values) and higher chromaticity (higher C value) were measured with the agents as contemplated herein.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Agent for dyeing keratinous material, comprising:
   (a1) at least one amino-functionalized silicone polymer,
   (a2) at least one color-imparting compound,
   (a3) at least one addition product of ethylene oxide to the esters of $C_{12}$-$C_{24}$ fatty acids and $C_1$-$C_{12}$ aliphatic alcohols, present in a total amount of from about 4 to about 8 weight % based on the total weight of the agent; and
   (a4) a fat constituent selected from the group of $C_{12}$-$C_{24}$ fatty alcohols, $C_{12}$-$C_{24}$ fatty acid triglycerides, $C_{12}$-$C_{24}$ fatty acid monoglycerides, $C_{12}$-$C_{24}$ fatty acid diglycerides and/or hydrocarbons, wherein the fat constituent is present in an amount of from about 3 to about 30 weight % based on the total weight of the agent.

2. The agent according to claim 1, wherein the at least one amino-functionalized silicone polymer (a1) has at least one secondary amino group.

3. The agent according to claim 1, wherein the at least one amino-functionalized silicone polymer (a1) comprises at least one structural unit of the formula (Si amino),

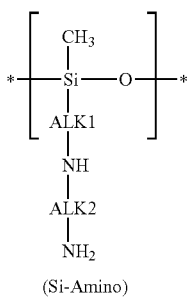

(Si-Amino)

where
ALK1 and ALK2 independently represent a linear or branched $C_1$-$C_{20}$ divalent alkylene group.

4. The agent according to claim 1, wherein the at least one amino-functionalized silicone polymer (a1) comprises structural units of the formula (Si-I) and of the formula (Si-II)

(Si-I)

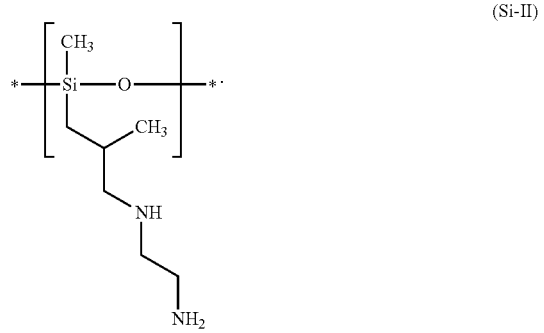
(Si-II)

5. The agent according to claim 1, wherein, based on the total weight of the agent, the least one amino-functionalized silicone polymers (a1) is present in a total amount of from 0.1 to 8.0 wt. %.

6. The agent according to claim 1, wherein the at least one color-imparting compound (a2) is selected from the group of pigments, direct dyes, photochromic dyes, thermochromic dyes or combinations thereof.

7. The agent according to claim 1, wherein the at least one color-imparting compound (a2) is selected from the group of colored metal oxides, metal hydroxides, metal oxide hydrates, silicates, metal sulfides, complex metal cyanides, metal sulfates, bronze pigments, colored mica- or mica-based pigments coated with at least one metal oxide and/or a metal oxychloride, or combinations thereof.

8. The agent according to claim 1, wherein the at least one color-imparting compound (a2) is selected from the group of carmine, quinacridone, phthalocyanine, sorghum, blue pigments with the color index numbers CI 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470, or combinations thereof.

9. The agent according to claim 1, wherein, based on the total weight of the composition (a), the color-imparting compound (a2) is present in a total amount of 0.01 to 10.0 wt. %.

10. The agent according to claim 1, wherein the at least one addition product of ethylene oxide to the esters (a3) is obtained by esterification of one, two or three $C_{12}$-$C_{24}$ fatty acids with glycerol.

11. The agent according to claim 1, wherein the at least one addition product of ethylene oxide to the esters (a3) comprises at least one ethoxylated fatty acid ester of the general formula (EFA-I)

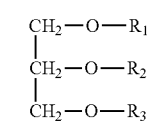
(EFA-I)

where
R1, R2, R3 independently represent a grouping —($CH_2$—$CH_2$—O)$_v$—H, or a grouping of the general formula (EFA-II),

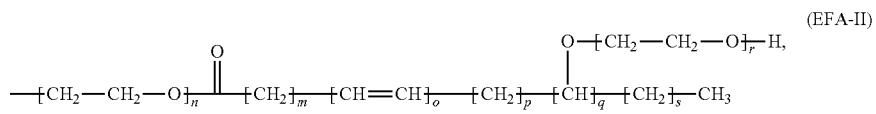
(EFA-II)

where
V represents an integer from 0 to 100,
n represents an integer from 0 to 100,
m represents an integer from 1 to 8,
o represents an integer from 0 to 3,
p represents an integer from 1 to 8,
q represents the number 0 or 1,
r represents an integer from 1 to 100, and
s represents an integer from 1 to 8,
provided that
at least one of the radicals R1, R2, R3 represents a grouping of the general formula (EFA-II), and in that
at least one of the index numbers for v, n and/or q is a number not equal to 0.

12. The agent according to claim 11, wherein the at least one addition product of ethylene oxide to the esters (a3) comprises the at least one ethoxylated fatty acid ester of the general formula (EFA-I)
where
R1, R2, R3 independently represent a grouping of the general formula (EFA-II),

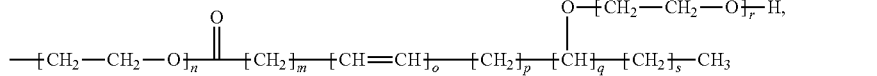

where
n represents the number of 0
m represents an integer from 1 to 8,
o represents the number 0 or 1,
p represents an integer from 1 to 8,
q represents the number 1,
r represents an integer from 1 to 100, and
s represents an integer from 1 to 8.

13. The agent according to claim 1, wherein the at least one addition product of ethylene oxide to the esters (a3) comprises at least one ethoxylated fatty acid ester selected from the group of PEG-5 Hydrogenated Castor Oil, PEG-10 Hydrogenated Castor Oil, PEG-20 Hydrogenated Castor Oil, PEG-30 Hydrogenated Castor Oil, PEG-40 Hydrogenated Castor Oil, PEG-50 Hydrogenated Castor Oil, PEG-60 Hydrogenated Castor Oil, PEG-70 Hydrogenated Castor Oil, PEG-80 Hydrogenated Castor Oil, PEG-90 Hydrogenated Castor Oil, PEG-100 Hydrogenated Castor Oil, PEG-5 Castor Oil, PEG-10 Castor Oil, PEG-20 Castor Oil, PEG-30 castor oil, PEG-40 castor oil, PEG-50 castor oil, PEG-60 castor oil, PEG-70 castor oil, PEG-70 castor oil, PEG-80 castor oil, PEG-90 castor oil, PEG-100 castor oil, or combinations thereof.

14. The agent according to claim 11, wherein the at least one addition product of ethylene oxide to the esters (a3) comprises the at least one ethoxylated fatty acid ester of the general formula (EFA-I)
where
R1, R2, R3 independently of one another represent a hydrogen atom, a grouping —(CH$_2$—CH$_2$—O)$_v$—H, or a grouping of the general formula (EFA-II),

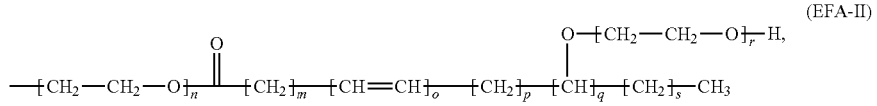

where
V represents an integer from 0 to 100,
n is an integer from 0 to 100,
m represents an integer from 1 to 8,
o represents the number 0,
p represents an integer from 1 to 8,
q represents the number 0,
s represents an integer from 1 to 8,
provided that
at least one of the radicals R1, R2, R3 represents a grouping of the general formula (II), and in that at least one of the index numbers for v and/or n is a number not equal to 0.

15. The agent according to claim 1, wherein the at least one addition product of ethylene oxide to the esters (a3) comprises at least one ethoxylated fatty acid ester selected from the group of PEG-7 glyceryl monolaurate, PEG-7 glyceryl monomyristate, PEG-7 glyceryl monopalmitate, PEG-7 glyceryl monostearate, PEG-7 glyceryl monocaprylate, PEG-7 glyceryl monocaprate, PEG-10 glyceryl monolaurate, PEG-10 glyceryl monomyristate, PEG-10 glyceryl monopalmitate, PEG-10 glyceryl monostearate, PEG-10 glyceryl monocaprylate, PEG-10 glyceryl monocaprate, PEG-5 glyceryl monolaurate, PEG-5 glyceryl monomyristate, PEG-5 glyceryl monopalmitate, PEG-5 glyceryl monostearate, PEG-5 glyceryl monocaprylate, PEG-5 glyceryl monocaprate, PEG-7 glyceryl cocoate, PEG-7 glyceryl dilaurate, PEG-7 glyceryl dimyristate, PEG-7 glyceryl dipalmitate, PEG-7 glyceryl distearate, PEG-7 glyceryl dicaprylate, PEG-7 glyceryl dicaprate, PEG-10 glyceryl dilaurate, PEG-10 glyceryl dimyristate, PEG-10 glyceryl dipalmitate, PEG-10 glyceryl distearate, PEG-10 glyceryl dicaprylate, PEG-10 glyceryl dicaprate, PEG-5 glyceryl dilaurate, PEG-5 glyceryl dimyristate, PEG-5 glyceryl dipalmitate, PEG-5 glyceryl distearate, PEG-5 glyceryl dicaprylate, PEG-5 glyceryl dicaprate, PEG-7 glyceryl cocoate, PEG-7 glyceryl trilaurate, PEG-7 glyceryl trimyristate, PEG-7 glyceryl tripalmitate, PEG-7 glyceryl tristearate, PEG-7 glyceryl tricaprylate, PEG-7 glyceryl tricaprate, PEG-10 glyceryl trilaurate, PEG-10 glyceryl trimyristate, PEG-10 glyceryl tripalmitate, PEG-10 glyceryl tristearate, PEG-10 glyceryl tricaprylate, PEG-10 glyceryl tricaprate, PEG-5 glyceryl trilaurate, PEG-5 glyceryl trimyristate, PEG-5 glyceryl tripalmitate, PEG-5 glyceryl tristearate, PEG-5 glyceryl tricaprylate, PEG-5 glyceryl tricaprate, PEG-7 glyceryl cocoate, or combinations thereof.

16. The agent according to claim 1, wherein, based on the total weight of the agent further comprises,
a total content of all anionic surfactants contained in the agent is below 0.1 wt. %, and
a total content of all cationic surfactants contained in the agent is below 0.1 wt. %.

17. The agent according to claim 1, wherein, based on the total weight of the agent further comprises,
a total content of all anionic polymers contained in the agent is below 0.1 wt. %, and
a total content of all cationic polymers contained in the agent is below 0.1 wt. %.

18. The agent according to claim 1, further comprising water, and wherein the agent has a pH of from 7.0 to 11.5.

19. A method for dyeing keratinous material, comprising the steps of:
(1) applying the agent according to claim 1 to the keratinous material,
(2) exposing the agent to the keratinous material for a period from about 30 seconds to about 15 minutes, and
(3) rinsing out the agent from the keratinous material with water.

* * * * *

UNITED STATES PATENT AND TRADEMARK OFFICE
CERTIFICATE OF CORRECTION

PATENT NO. : 11,865,201 B2
APPLICATION NO. : 17/762655
DATED : January 9, 2024
INVENTOR(S) : Constanze Kruck et al.

It is certified that error appears in the above-identified patent and that said Letters Patent is hereby corrected as shown below:

In the Specification

Column 5, Line 66-67 change "3-1(2-aminoethypaminol-2-methylpropyl Me" to
--3-[(2-aminoethyl)amino]-2-methylpropyl Me--.
Column 8, Line 7 change "NH(CH$_2$)$_z$(CH 2)$_{zz}$NH" to --NH(CH$_2$)$_z$(CH 2)$_{zz}$NH--.
Column 21, Line 12 change "represents an integer" to --o represents an integer--.
Column 22, Line 66 change "represents the number" to --o represents the number--.
Column 23, Line 21 change "represents the number" to --o represents the number--.
Column 24, Line 41 change "represents the number" to --o represents the number--.
Column 25, Line 13 change "represents the number" to --o represents the number--.
Column 25, Line 63 change "CH$_2$-CH$_2$-O" to --CH2-CH2-O--.
Column 32, Line 31 change "C$_{10}$-30" to --C10-30--.
Column 32, Line 33 change "C$_{10}$-30" to --C10-30--.
Column 32, Line 35 change "C$_{12}$-22" to --C12-22--.
Column 34, Line 63 change "hydroxy cinnamic acids" to --hydroxycinnamic acids--.
Column 38, Line 3 change "ad" to --and--.

Signed and Sealed this
Twenty-third Day of April, 2024

Katherine Kelly Vidal
*Director of the United States Patent and Trademark Office*